United States Patent [19]

Butler et al.

[11] Patent Number: 4,801,805

[45] Date of Patent: Jan. 31, 1989

[54] METHOD OF MEASURING MULTICOMPONENT CONSTITUENCY OF GAS EMISSION FLOW

[75] Inventors: James W. Butler, Dearborn Heights; Paul D. Maker, Ann Arbor; Thomas J. Korniski, Livonia; Alex D. Colvin, Oak Park, all of Mich.

[73] Assignee: Ford Motor Company, Dearborn, Mich.

[21] Appl. No.: 87,171

[22] Filed: Aug. 19, 1987

[51] Int. Cl.$^4$ .......................................... G01N 21/37
[52] U.S. Cl. ..................................... 250/343; 250/341
[58] Field of Search ...................... 250/338.5, 339, 340, 250/341, 343, 352; 356/437, 439

[56] References Cited

U.S. PATENT DOCUMENTS

| | | | |
|---|---|---|---|
| 3,897,154 | 7/1975 | Hawes | 250/345 |
| 4,227,083 | 10/1980 | Sherinski | 250/343 |
| 4,549,080 | 10/1985 | Baskins et al. | 250/343 |
| 4,652,755 | 3/1987 | Solomon et al. | 250/341 |

OTHER PUBLICATIONS

SAE Paper #810429 (1981), "On-Line Characterization of Vehicle Emissions by FT-IR and Mass Spectrometry", Butler et al.

*Primary Examiner*—Janice A. Howell
*Attorney, Agent, or Firm*—Joseph W. Malleck; Roger L. May

[57] ABSTRACT

A method is disclosed of making an on-line gas analysis of a multicomponent gas emission flow by (a) continuously sequestering a sample flow from the gas emission flow, which sample flow has been filtered to substantially eliminate solid or liquid particles, diluted to lower its dew point to below room temperature, and changed in either temperature and/or pressure to be substantially the same in temperature and pressure as that of gases used to create reference transmission frequency spectral data deployed in step (d); (b) continuously irradiating the sample flow with an electromagnetic radiation beam while modulating the amplitude of infrared frequencies in the audio frequency range of the beam, either prior to or immediately subsequent to irradiation of the sample flow, to produce electromagnetic signals having discernible amplitude variations resulting from spectral interference patterns; (c) detecting and collecting the signals at a sufficiently high rate to substantially completely distinguish between adjacent spectral pattern amplitude peaks without mutual spectral interference and to permit analysis of the signals in real time; and (d) analyzing the signals in real time by (i) mathematically manipulating the signals in accordance with Beer's Law to create reformed background-corrected data, and (ii) applying reference transmission frequency spectral data to the reformed data for each suspected gaseous component to give a linear quantitative measure of the presence of each and every suspected gas component in the gas emission flow.

25 Claims, 5 Drawing Sheets

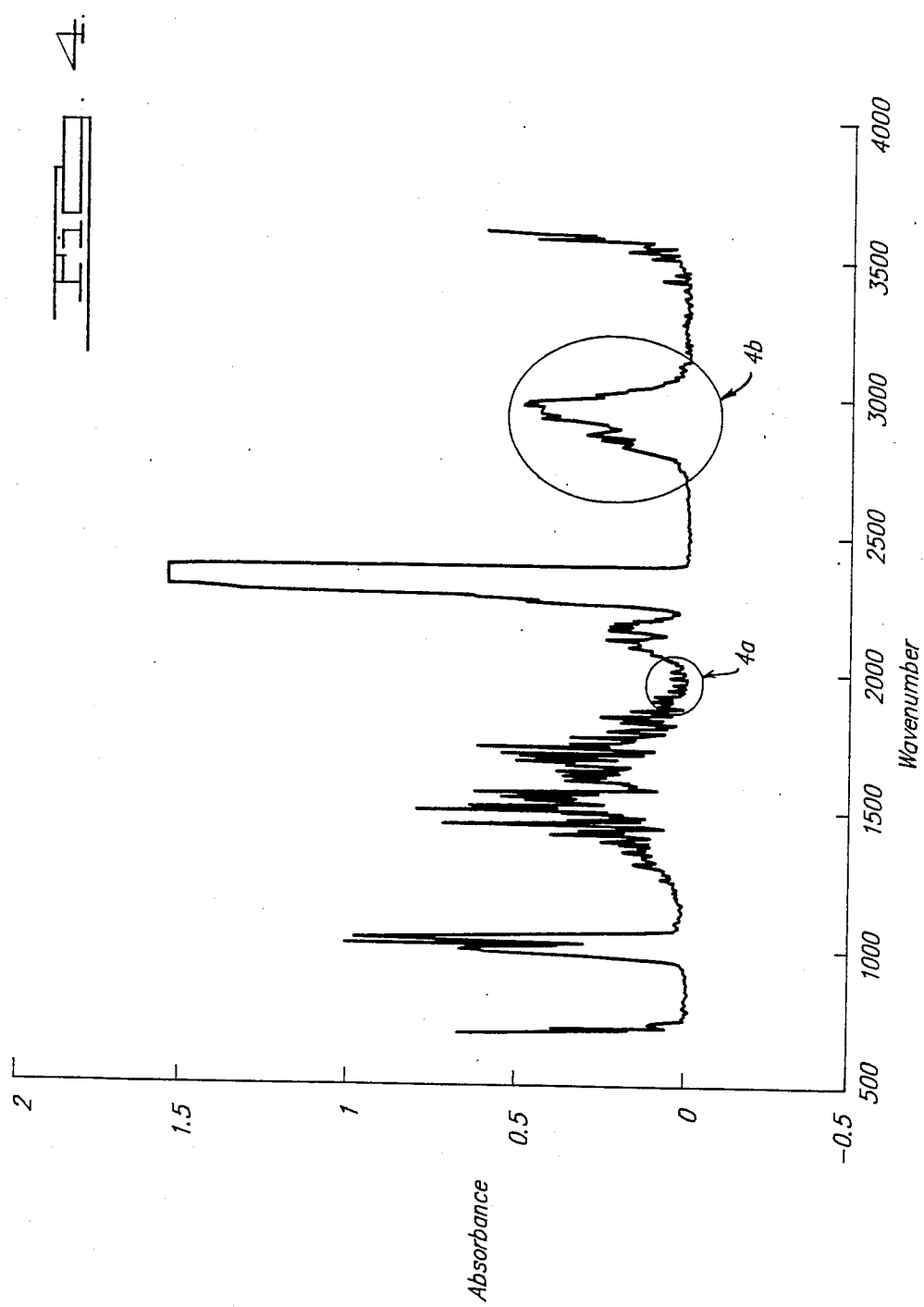

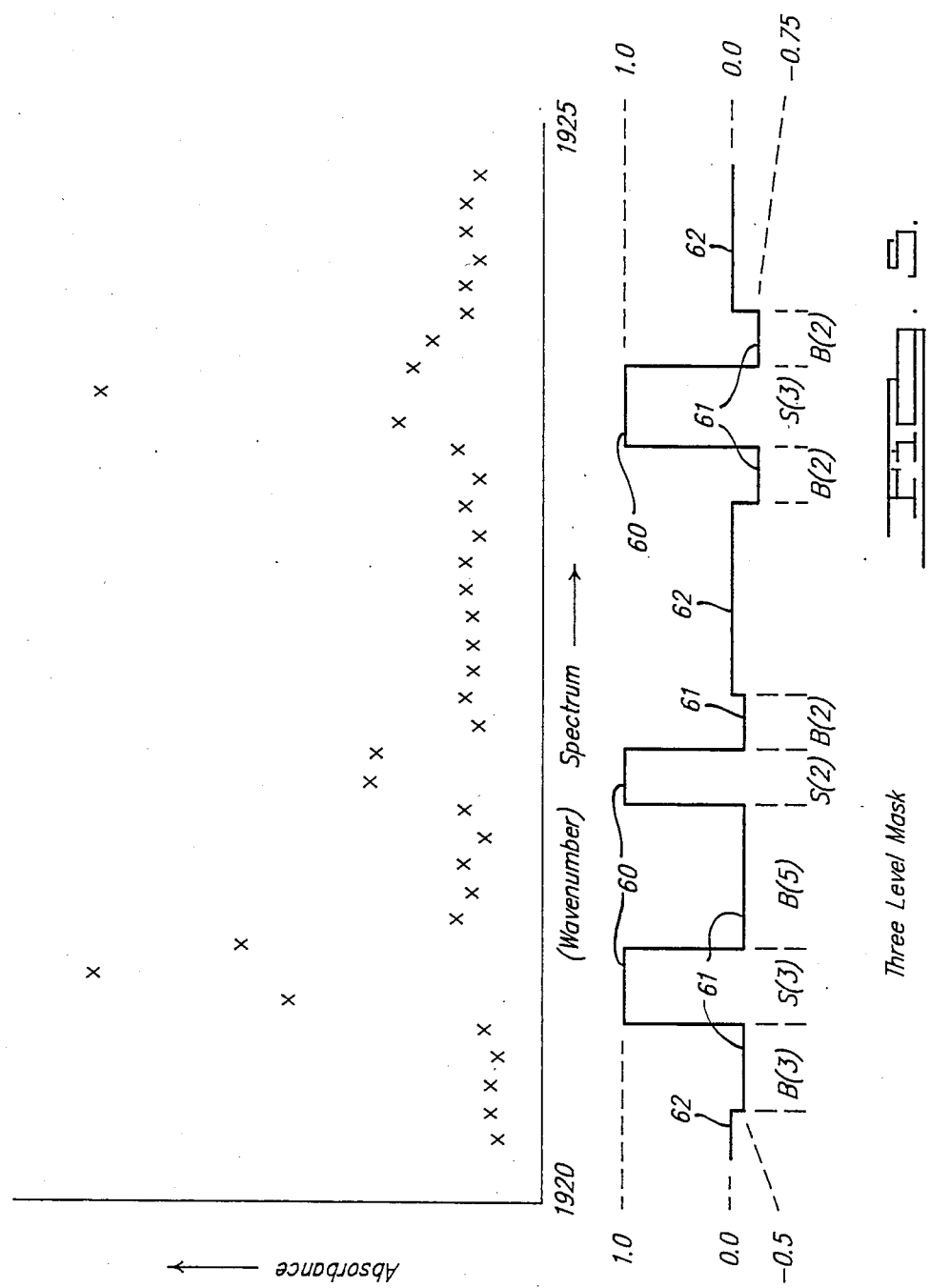

METHOD OF MEASURING MULTICOMPONENT CONSTITUENCY OF GAS EMISSION FLOW

BACKGROUND OF THE INVENTION

1. Technical Field

This invention relates to the art of gas analysis and, more particularly, to instantaneous on-line analysis of gas flows having multicomponents.

2. Description of the Prior Art

Gas analysis has wide ranging utility, from the measurement of respiration of humans or animals to the measuremetn of the effluence of combustion chambers, including automotive emissions. Gas analysis has conventionally been accomplished by the use of dilution tubes and by the use of liquids or solids off-line from the flow of gases under analysis. These techniques are inadequate fro modern purposes because of the inability to provide instantaneous dynamic information and measure only a single component per technique. These techniques are unable to process increasingly larger volumes of data.

Analyses without liquids or solids have included chemiluminescence, flame ionization, and total hydrocarbon analysis, all without the use of infrared spectroscopy. These modes have proved inadequate because (a) the analysis is of a single component, (b) takes too long, sometimes weeks, (c) the data for separate components has no commonality in response time and thus cannot be readily combined, (d) the sensed data suffers from cross-interferences of the added chemicals, and (e) some gaseous compounds cannot be analyzed.

One of the most recent adaptation for gas analysis has been the use of infrared spectroscopy. Although infrared specftroscopy has been used as a quality control technique to obtain information on the composition of chemical products for many years, it has been used essentially off-line and primarily for measurement of nongases. Samples are typically prepared as thin films or solutions and measured in a quality control room with a laboratory instrument. Unfortunately, inherent time delays between actual material production and analytical results can typically range from a few hours to several days, which can result in costly waste and production of unacceptable material. Fourier-transform, infrared spectrometric techniques have been applied to particles suspended in gas flows (see U.S. Pat. No. 4,652,755).

In those prior art applications where infrared spectroscopy was applied to gas analysis, there was no dilution of the gas sampler and therefore the gas itself had to be heated to a temperature in excess of 100° C. to accommodate samples with high water vapor. If other reference information was applied to such detected information, the reference information had to be taken at identical elevated temperatures, which made the entire methodology extremely complex, delicate and difficult to calibrate. In U.S. Pat. No. 4,549,080, filters were used to look at isolated wavelengths, again without dilution.

The task of measuring emissions from vehicles has become increasingly more difficult. Demands for lower detection limits have arisen from the development of more efficient catalytic converters. Greater versatility is required for work with alternate fuels as new and as yet uncharacterized gas species are encountered. In addition to these requirements, a need for more efficient engines with lower emission rates necessitates the development of fast, on-line instrumentation, capable of analysis during transient engine operation. Such new analysis will permit in-depth examination of the combustion process in lieu of the current cumulative information obtained from conventional emissions instrumentations having expensive exhaust handling equipment including constant volume sampling.

The inventors herein have applied infrared spectroscopy to the on-line analysis of gases, particularly auto emissions. Our earlier work, as described in scientific publication "On-Line Characterization of Vehicle Emissions by FTIR and Mass Spectrometry", Butler et al, SAE Paper #810429 (1981), describes a system for dynamic analysis of vehicle emissions; the analysis system was comprised of a fourier transform, infrared spectrometer, a quadropolemass spectrometer, and a total hydrocarbon analyzer. Although it allowed on-line measurement of regulated and nonregulated emissions from a steady-state gas stream, the system needed to be calibrated with some difficulty. The three major apparatus components were significantly expensive; but, most importantly, an unusually large size, constant volume sampling apparatus was required for dilution of the sample gas. The speed at which such an integrated system operated was at the rate of three second. However, the data was analyzed off-line, rendering an analysis not in real time (while the test if on-going). This introduces an analysis time which is not considered sufficiently fast for the demands of new applications. It the total hydrocarbon analyzer, quadropole mass spectrometer, and constant volume sampling unit could be eliminated, the cost of the system would be significantly reduced. If the remaining components could be improved in response time, the speed of data collection could be increased significantly. Furthermore, if the data could be processed in real time (during the test), the utility of information would be greatly enhanced because adjustments can be made immediately and effects of the adjustments can be seen.

SUMMARY OF THE INVENTION

A principal object of this inventino is to provide an improved gas analysis method and a simplified, unique combination of elements that would eliminate the need for extended apparatus such as mass spectrometers, air/fuel ratio sensors, and hydrocarbon analyzers while, at the same time, generating extremely high resolution, high volume spectral data, and extremely fast speeds for measuring and exhibiting data on a myriad of gaseous components in real time.

Another object of this invention is to provide an improved gaseous sampling device that eliminates water condensation contamination and ensures proportionality of mass flow rate of the sampled gas.

Still another object of this invention is to provide an improved on-line measuring apparatus for multicomponent gas emission flows, the apparatus being characterized by improved data collection speed, greater freedom from false or interference data, and is much less costly to fabricate.

The method steps of this invention comprise: (a) continuously sequestering a sample flow, from a gas emission flow, the sample flow bing (i) filtered to substantially eliminate solid or liquid particles, (ii) diluted sufficiently to lower the dew point of such sample flow to below room temperature, and (iii) changed in either temperature and/or pressure to be substantially the same in temperature and pressure as that of gases used to create reference transmission frequency spectral data; (b) continuously irradiating the sample flow with an electromagnetic radiation beam, while modulatin the amplitude of infrared frequencies in the audio frequency range of the beam either prior to or immediately subsequent to irradiation of the sample flow to generate electromagnetic signals having discernible amplitude variations resulting from spectral interference patterns; (c) detecting and collecting said signals at a sufficietnly high rate to substantailly completely distinguish adjacent spectral pattern peaks without mutual spectral interference and to permit analysis of the siganls in real time; and (d) analyzing the signals in real time by (i) mathematically manipulating said signals in accordance with Beer's Law to create reformed background corrected data, and (ii) applying reference transmission frequency spectral data to the reformed data for each suspected component to give a linear quantitative measure of the presence of each and every suspected gas component in the gas emission flow. Beer's Law is often recited as:

$$\frac{I}{I_o} = l^{-[\alpha \cdot s(f)]}$$

where
I = intensity of light coming out of absorbance cell
$I_o$ = intensity of light going into absorbance cell
l = gase of natural log, i.e., 2.71828
α = particle density x pathlength
s = absorbance spectrum
f = frequency or wavenumber More particularly, step (b) advantageously comprises continuously irradiating the sample flow with a light beam, splitting the partially absorbed beam emerging from the sample flow into portions, sending one portion over a fixed length and the other over a variable length determined by movement of a mirror over a predetermined stroke, and recombining the beam portions to generate light signals resulting from spectral interference patterns. More particularly, step (c) preferably comprises detecting and collecting the signals at a minimum of 8000 measurements per each centimeter of path length difference of the beam and for a minimum of 4cm of path length difference. More particularly, step (d) advantageously comprises mathematically manipulating the signals by (i) converting an interval of detected signals to base transmission frequency spectrum data, (ii) rationing known background transmission frequency spectral data to the base data and taking the negative data, (iii) subtracting reference transmission frequency spectral absorbance data, for each suspected component, from the reformed absorbance spectral data to render a component concentration per unit time interval. If desired, the concentration values can be converted to mass per mile units by dividing the mass flow rate of the sequestered sample flow into the concentration value to render a mass per unit of time or engine usage.

Preferably, the sample flow is made proportional to the main emission flow's mass flow rate. Such proportionality of the sample flow can be achieved by placing a laminar flow element across the main flow as well as placing a laminar flow element across the sample flow. Dilution may preferably be achieved by admitting nitrogen gas into the sample over a flow ratio range of 5:1 to 70:1.

Preferably, the mathematical conversion step is carried out by the use of fourier-transform to provide transmission frequency spectral data. To achieve interference-free signals, reference data consisting principally of maximum/minimal signal frequency regions for a specific component is used to extract concentration information from the expanded spectral data.

SUMMARY OF THE DRAWINGS

FIGS. 4, 4a and 4b are graphical representations of absorbance data against wavenumber after applying Beer's Law; and FIG. 5 is a graphical representation of absorbance data plotted against wavenumber showing a spectral mask for $NO_x$ developed from the data points in a spectrum of points from 1920–1925.

DETAILED DESCRIPTION AND BEST MODE

Obtaining Gas Sample

The first step of the process comprises continuously sequestering a sample of the gas emission flow and affecting the sample flow to make it (i) filtered so as to be substantially devoid of solid or liquid particles, (ii) proportional to the mass flow rate of the gas emission flow, (iii) diluted sufficiently to lower the dew point of the sample flow to below room temperature, and (iv) changed in temperature and pressure to substantially the same temperature and pressure at which reference data was collected. Preferably, the reference data is collected at room temperature and at a pressure of 700 Torr; this will usually necessitate cooling of the sample gas flow to achieve.

Figure 1:
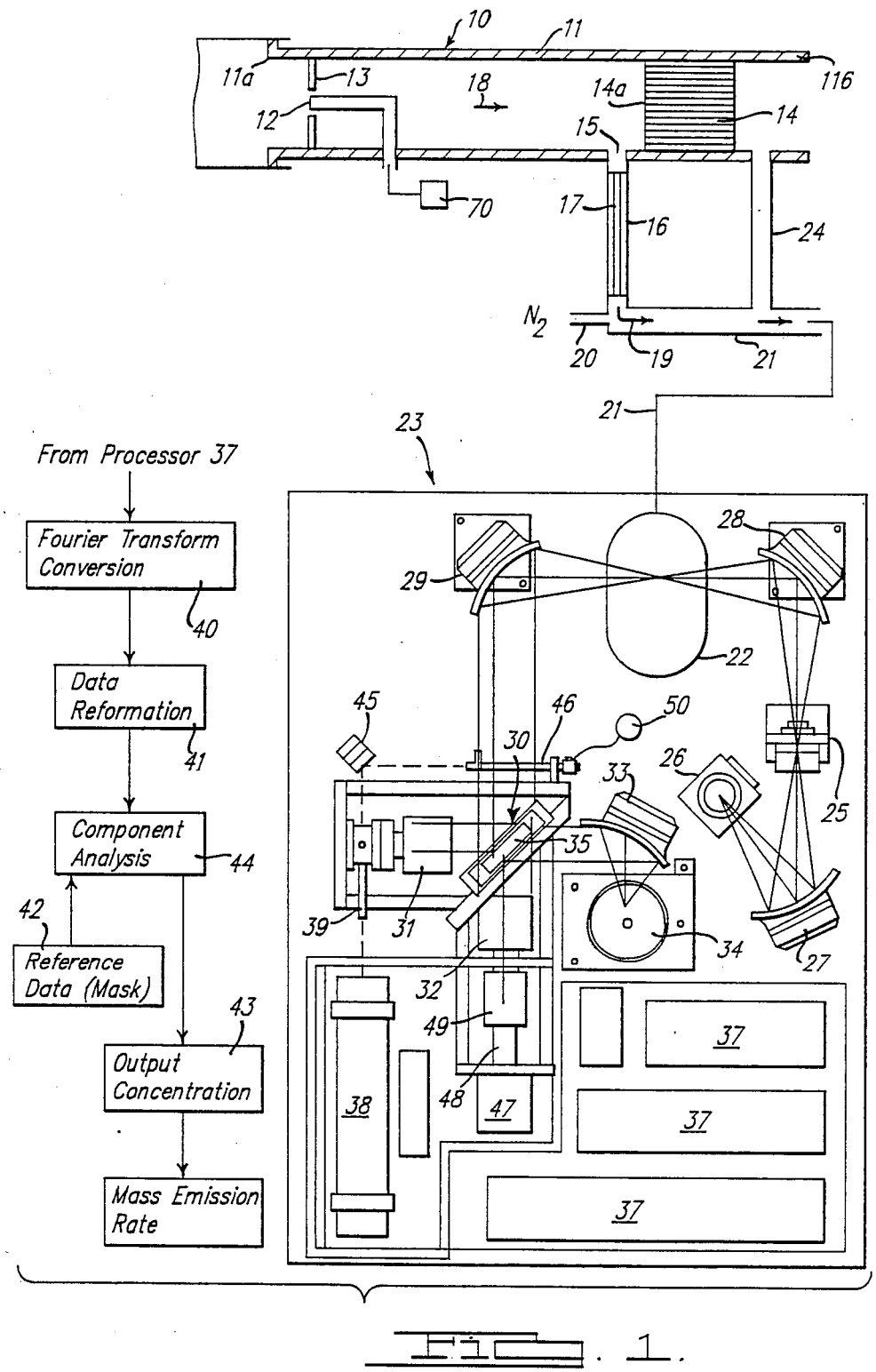
FIG. 1 is a schematic illustration of the apparatus components effective to carry out the steps of the method of this invention and depicts a novel gas sampling device and displays a unique appartus combination for the total gas analysis measuring system.

As shown in FIG. 1, a sampling device 10 is used to carry out these functions. The device comprises a stainless steel tube 11, preferably having an internal diameter of about 2¼ inches and a length of about 3 feet, preferably no greater than 4 feet. At the entrance or upstream end 11a of such tube (which is connected to the tailpipe or exhaust of an engine), an inlet 12 is located for introduction of a tracer gas, preferably carbon tetrafluoride; the tracer gas is injected at a known rate such as, for example, 10 cubic centimeters per minute. The inlet 12 may have a throat diameter of about ⅛ inch and is directed countercurrent to the main exhaust flow and is coplanar with the baffle 13 to achieve thorough mixing. The necessity for the injection of a tracer gas is to make possible the measurement of exhaust mass flow independent of fluctuations in the main emissions flow.

The tractor gas and emissions flow together, pass through the main body of the tube, are mixed, such as by baffle 13, and encounter a main laminar flow element 14 extending across the main flow 18 and across the internal extent of tube 11. The element 14 permits backpressure to increase in the main flow in response to an increase in mass flow. A sampling outlet 15 is provided adjacent the frontal face 14a of the main laminar flow element. The sampling passage 16 also contains a laminar flow element 17 extending across the sampling flow 19. A passage 21 carries the diluted flow to a cell 22 of an infrared optical apparatus 23. A passage 24 is connected across passage 21 and the outlet end 11b of the tube 11 to set up the same pressure differences to allow the sample to be withdrawn. The downstream pressure of both laminar flow elements 14 and 17 are substantially identical, thus the fraction sampled is proportional to the rate of the conductance of the two laminar flow elements.

The sampled flow 19 is then diluted by admission of a dilution gas, such as nitrogen, having a purity of 99.9%, from an inlet at 20 and admitted, preferably, at a rate of about 30 liters per minute so as to dilute the sample flow in a ratio ranging from about 5:1 to a ratio of 70:1. Dilution is significant because it eliminates condensation and allows the test to take place at substantially atmospheric conditions (preferably 700 Torr), thus minimizing pressure effects on the infrared spectrum and allowing calibration using a preexisting reference data base.

IRRADIATION

The diluted sample flow in the cell 22 is then continuously irradiated by being subjected to an infrared light source to provide test spectral data. This is accomplished by use of an infrared optical apparatus 23, such as shown schematically in FIG. 1, wherein through an optical analysis module arrangement, the infrared light source 26 is directed by mirror 27 through an iris aperture 25 and then again by mirror 28 through the cell 22 of a sampling module containing the diluted sample gas flow. The partially absorbed beam, emerging from cell 22, is directed by mirror 29 into a beam splitter 30. The beam is split at unit 35 into two portions, one portion is reflected by the splitter to traverse a fixed distance or length, into corner-cube mirrors 31 and return to splitter 30 and pass through the splitting unit 35. The other beam part is allowed to pass through unit 35 and traverse a variable length determined by movement of a sliding or stroked corner-cube mirror 32. The corner-cube mirror 23 is moved by a linear magnetic motor 47 operating on a shaft 48 attached to the mirror 38 through a bearing 49. The extent of the mirror cube stroke determines the deviation of the other beam part from the first beam part. The deviated and nondeviated beam parts are recombined by unit 35 to form light signals resulting from spectral interference patterns.

To sense the movement of the movable corner-cube mirror 32 and determine when to measure detected signals, a helium-neon laser fringe system 38 is used. The beam emitted from the source at 38 passes through an alignment device 39 associated with fixed corner-cube mirror 31 and thence is directed by mirror 45 to pass into alignment device 46 associated with the movable corner-cube mirror 32. A detector 50 senses the difference or variance from zero alignment between the mirrors and thus senses the location and movement of movable corner-cube mirror 32.

The apparatus 23 differs from conventional grating or prism instruments in that wavelength determination is accomplished by modulating the amplitude of each wavelength of the emitted radiation at its own unique audio range frequency via a scanning Michelson interferometer. The interferometer used as a Mattson SIR-IUS 100, equipped with a KBr/Ge beam splitter. The light source was a conventional ceramic glower emitting a broad band infrared radiation, which is close to white light (the latter having all frequencies generally intense). The cell 22 was a Wilks 20 meter variable path cell used in the 14th order resulting in an effective pathlength of 21.75 meters.

Deviation is used herein to mean the amount of mirror travel or stroke used in splitting off a part of the light beam for developing spectral interference patterns. Spectral interference pattern is used herein to mean the intensity fluctuations imposed on the original beam radiations by the movement of the stroked mirror. An interference pattern results from use of an interferometer giving amplitude modulation of each radiation wavelength at its own unique audio range frequency.

DETECTION

The light signals resulting from spectral interference patterns are directed by mirror 33 to a detector 34 (a liquid nitrogen cooled HgCdTe photoconductor). The spectral emissions are received by the detector on a continuous basis and are converted to an analog voltage. The amplified voltage signals, being a linear measure of the changes in the detector conductivity, are digitized using a computer processor 37. To obtain higher resolution with high volume spectral data eminating from a multicomponent gas emission flow, the detector must detect and collect the light signals (as changes in detector conductivity) at a minimum of 8000 measurements per each centimeter of path length difference and for a minimum of 4 cm of path length difference to create a spectrum of data. This large spectrum of data in a very short interval permits this process to substantially completely distinguish adjacent spectral pattern peaks without mutual spectral interference. A measurement of the detector output voltage is made at uniform spacings during the 4 cm of stroke (at substantially the wavelength of the helium-neon laser). Distinguishing adjacent spectral peaks means employing a long enough corner cube mirror stroke to produce derived spectral patterns with 0.25 cm$^{-1}$ (wave per centimeter) spectral line widths.

The signals were collected during a three second interval by forming an interferogram and writing the interferogram onto computer memory in computer processor 37. The interval (which was three seconds) was determined by the period needed to fully process the spectral data. The detector receives the spectral emission signals aas analogue signals per unit of time or interval, and are converted to continuously varying digital signals per unit of time and stored in the computer memory. The signals are received by the detector at a rate of at least 32,000 data points in a three second interval during sweep of the sliding corner cube mirror over a 4 cm path length.

MATHEMATICAL CONVERSION

The ability to detect and record such a high accumulation of data points in such a short period of time is made possible by the use of a multiprocessor computer 40-41-44 having multimemory feed paths. More specifically, the multipath accomplished the following. While incoming signals are being recorded and stored (i) the previously stored signals can be simultaneously fourier-transformed to yield spectral signals in computer 40, (ii) the transformed signals can be reduced to gaseous component concentration values in computers 41-44, and (iii) the computed values can be displayed on a veiwing apparatus. All of this is accomplished in real time.

Figure 2:
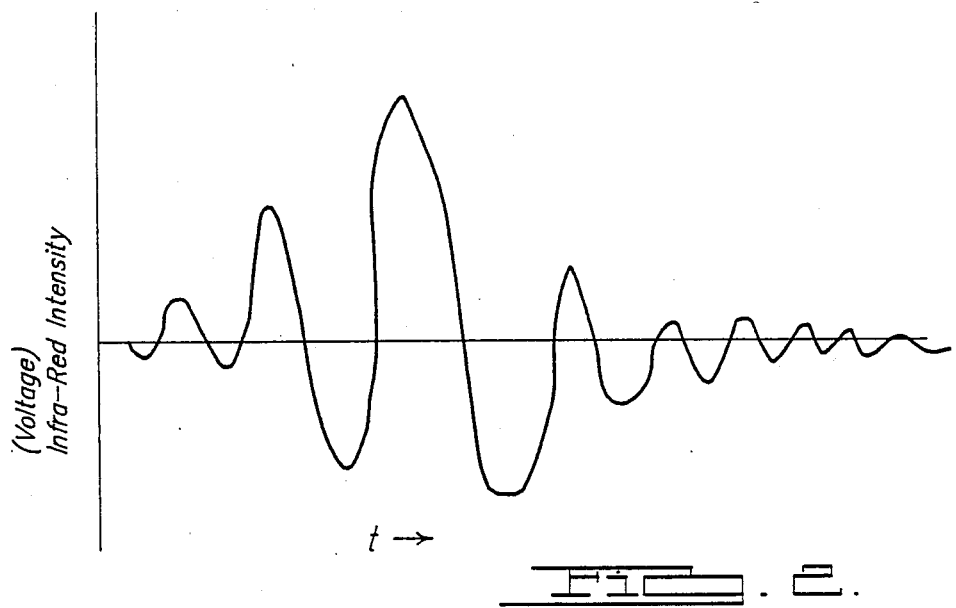
FIG. 2 is a graphical representation of voltage signals plotted against time, such signals eminating from the interferogram.
Figure 3:
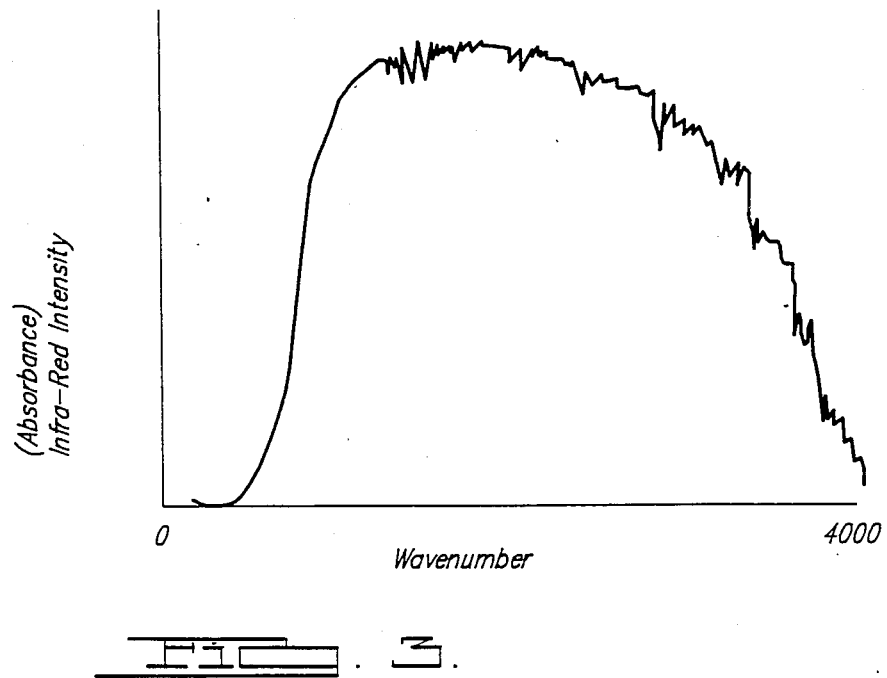
FIG. 3 is a graphical representation of absorbance data plotted against wavenumber eminating from fourier-transform.

In the first stage of mathematical conversion, a spectrum or an interval of the detected signals from spectral interference patterns (interferogram as shown in FIG. 2) is converted to infrared intensity (absorbance) data varying with wavenumber (frequency) as shown in FIG. 3. This is carried out by the use of fourier-transform techniques programmed in computer 40. A detailed description of such techniques used in computer 40 is given in "Introductory Fourier-Transform Spectroscopy", by R. J. Bell, Academic Press, New York (1972). Frequency analysis or fourier analysis of the digitally recorded interferogram leads to the wavelength dependence of the infrared intensity, the infrared spectrum. The use of the fourier-transform spectroscopic method offers great speed advantages when dealing with the very high resolution spectra needed for the quantitative analysis of gas mixtures. FTIR is sometimes used herein to mean the operations carried out by apparatus 23 and computer 40.

To increase the speed of electronic assimilation of such high volume/rate signals, an array processor was used as part of the multiprocessor computer 40. The multiprocessor computer also comprised a Mass comp minicomputer 2M Byte memory, 85M Byte Winchester disks, 1.2M Byte floppy disks, and a 40M Byte magnetic tape system to handle the data processing display and archiving. The software package included a special purpose, fast fourier-transform routines for comparing, combining, displaying, plotting, analyzing and otherwise manipulating spectral files.

The resulting intensity-frequency data (as shown in FIG. 3) was corrected (within electronic computer means 41 for data reformation) for the contribution of room temperature stray radiation by referencing a previously determined room temperature background. A reformed absorbance spectrum was thus generated by calculating the negative logorithm of the ratio of corrected known transmission spectrum of the dilution air backgroun (i.e., taken at 700 Torr and room temperature for the dilution tube air in the cell) to the corrected transmission spectrum of the sample. This eliminates effects of $CO_2$, $H_2O$, and trace hydrocarbons in the ambient air.

Figure 4A:
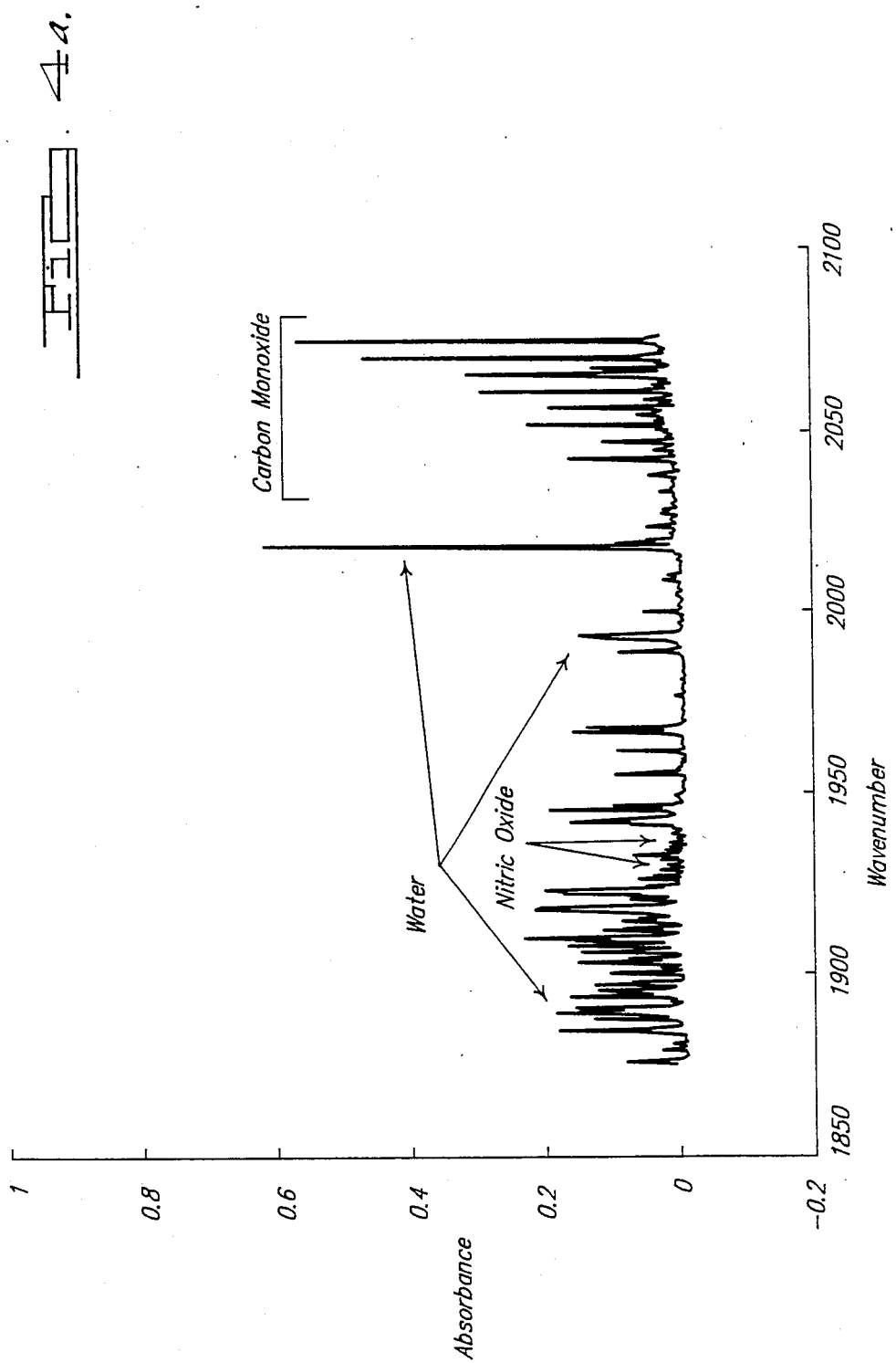
Figure 4B:
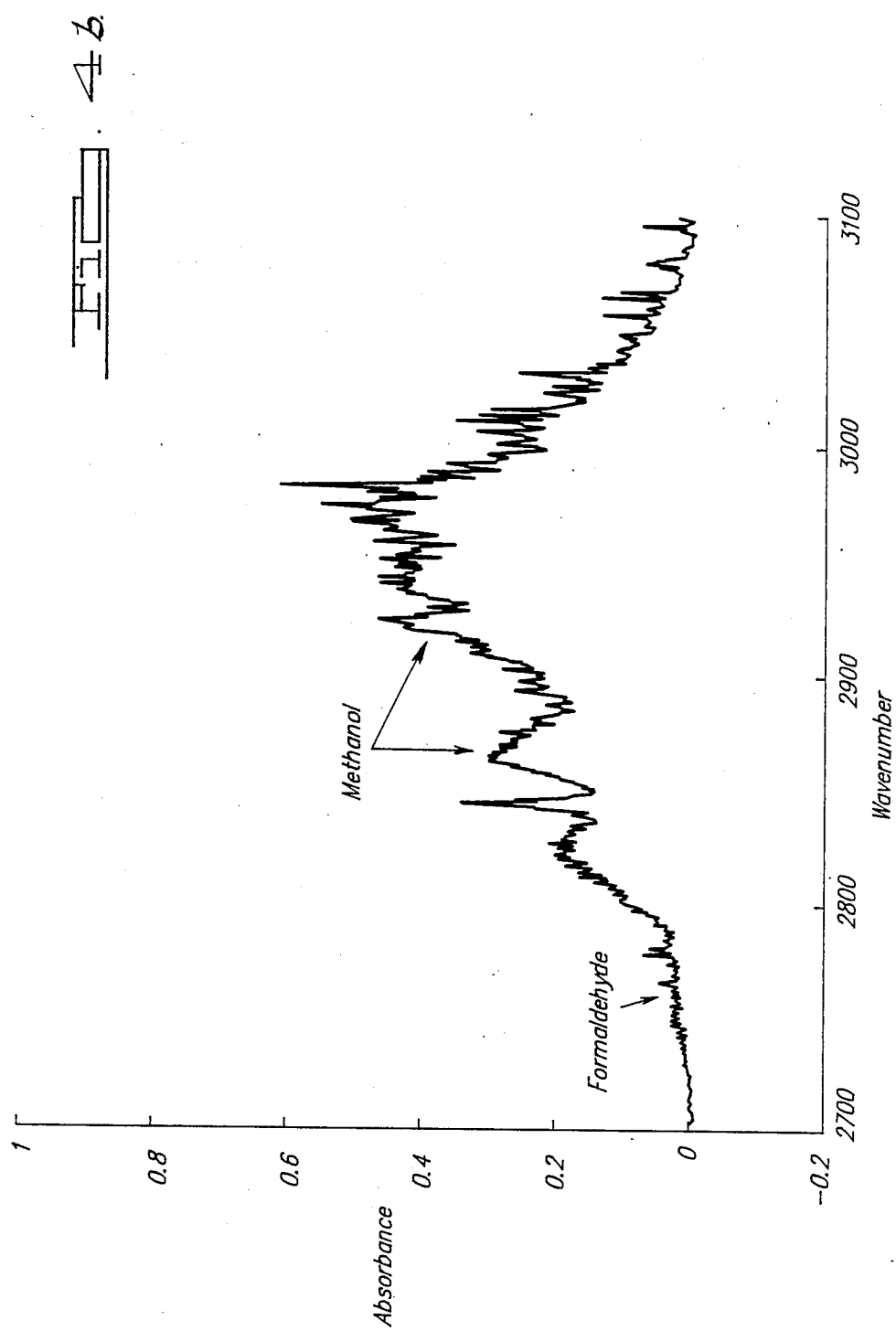

The resulting reformed absorbance spectra (as shown in FIG. 4) were then analyzed for components of interest by computer 44. The difficulty of analyzing simply the reformed absorbance data to arrive at a concentration value is demonstrated in FIGS. 4a and 4b. It should be noted that for these absorbance spectra, Beer's Law implies that the gas component concentration is linearly related to the spectral line strength. Only by considerable expertise can the spectral line strengths be identified as a specific gas species. To add the line strengths to arrive at a concentration value is fraught with difficulty.

To analyze for components of interest by this invention, reference masks data (contained electronically in computer means 42) are applied to reformed absorbance data (the room temperature corrected spectral information) in computer 44 for each suspected component to render a component concentration.

A mask is explained as follows and by reference to FIG. 5. A linear measure of the concentration of a gas is given by the strength of a line in its true absorbance spectrum. When noise is present in the spectrum, a more reliable measure is provided by summing the strengths of many lines. Such measure is also provided by the height of a narrow line projecting above a broader absorbance feature. The area under the absorbance curve or trace is the measure of the gas species. The method of approximating the area under such curve is speeded up by use of linear algebra in the form of masks. A simulated spectrum or "mask" is prepared consisting of segments 60 made up of 1.0's at spectral positions corresponding to narrow absorbance lines (spectral regions of strong, but not saturating unique absorption for that gas species), segments 61 made up of several small negative fractions at positions surrounding the 1.0's, and segments 62 made up of zero elsewhere. The negative fractions (segments 61) have value (number of 1.0's)/(sum of negatives) and correspond to adjacent localized, nonabsorbing spectral regions. Their purpose is first to establish the average base level above which the narrow line protrudes, and then used to subtract that level from each of the 1.0's. The above sum can then be computed by multiplying together the spectrum from computer 41 (FIG. 4) and the mask, i.e., taking their "dot" product, regarding them to be vectors. This task is accomplished very quickly by the computer's "array" or "vector" processor, particularly if spectal regions where the mask is zero are ignored entirely. The constant or proportionality relating the sum and the concentration of the gas can be determined by employing gases of known concentration, i.e., "standard" gases.

To analyze a mixture of gases, the mask for each species present is applied to the absorbance spectrum of the mixture. For the ideal case in which (mask of gas A) x (spectrum of gas B)=0 for A=B, the result, upon applying the known constants of proportionality, gives directly the quantitative composition of the sample gas. In practice, the masks are not ideal, but interferences can be accounted for since the response of each mask to the spectrum of each pure gas is known.

The construction of such masks depends upon the availability of a library of reference absorbance spectra for all gases comprising the mixture to be analyzed, in a concentration near that at which they are present in the mix. Each mask is prepared manually with constant referral to the library, the need to maximize response to the subject gas being weighed carefully against introduction of either interferences from other species or unwanted noise. The partial mask was made up of only the essential or unique spectral distinguishing feature points of a known gas species. This step was calibrated to give actual concentration values by applying the partial mask to the spectrum of a carefully selected and prepared standard sample of known concentration.

Individual masks were manually constructed for the best mode by a computer operator from a reference spectrum of a molecule of interest using as guides, in the choice of unique absorption bands, both the spectrum of the exhaust sample to be measured and reference spectra of all other molecules suspected of being present. Separate sets of masks were prepared to handle each of the various combinations of species in concentrations encountered in different experiments. A response matrix was then generated for each set of masks by applying each mask successively to the reference spectrum of each of the molecules respresented in that set. Ideally, this would be a unit matrix, but inevitably the masks were imperfect. Such imperfections were eliminated from the final result by multiplication with the inverse of the appropriate response matrix, all in accordance with the prescriptions of linear response theory. The summation value generated by component analysis in computer 44 can be displayed in unit 43.

When a sample is introduced by means of the sampling system shown in FIG. 1, the mass emission rates are preferably obtained by combining the component signal with the signal strength of the carbon tetrafluoride signal and dividing by the mass injection rate of the carbon tetrafluoride tracer.

More specifically, the exhaust mass flow of the engine may be computed by measuring the equivalence ratio as taught in U.S. Pat. No. 4,389,881 and combining this measurement with the hydrogen carbon ratio of the fuel, the oxygen carbon ratio of the fuel, the carbon dioxide fraction in the diluted sample as measured by FTIR, the carbon tetrafluoride mass injection flow, and the carbon tetrafluoride fraction in the diluted exhaust as measured by FTIR. The following illustrates mathematically how this is carried out.

EXHAUST GAS FLOW (BASED ON MINI-CVS)

Lean Case ($\lambda \geq 1$):

$$X = \frac{YD}{W}\left[\frac{N}{4} + \frac{P}{2} + \frac{\lambda}{0.21}\left(1 + \frac{N}{4} - \frac{P}{2}\right)\right]$$

Rich Case ($\lambda < 1$):

$$X = \frac{YD}{W}\left[\frac{1 + N/2 + 3.96\lambda(1 + N/4 - P/2)}{1 - [(1 - \lambda)(1 - N/4 - P/2)]\,3/2}\right]$$

where

N = hydrogen/carbon ratio of fuel (no units)
P = oxygen/carbon ratio of fuel (no units)
$\lambda$ = oxygen equivalence of exhaust gas (no units)
Y = $CO_2$ fraction in final diluted sample (measured by FTIR (no units)
D = $CF_4$ tracer flow (STP volume/time)
W = $CF_4$ fraction by FTIR (no units)
X = engine exhaust flow (STP volume/time)

Alternately, the mass emission rate is determined by sampling from a dilution tube and by first obtaining the average dilution tube flow (in scfm) for each test by use of a flowmeter 70. This tunnel flow was then converted to liters per three seconds to match the time interval of the FTIR data interval. Based on the tunnel flow and the concentration data, the emissions in milligrams per three second interval are computed for each gaseous component.

Table I shows an actual computer listing of compound concentrations obtained from testing as identified.

While particular embodiments of the invention have been illustrated and described, it will be noted by those skilled in the art that various changes and modifications may be made without departing from the invention, and it is intended to cover in the appended claims all such modifications and equivalents as fall within the true spirit and scope of the invention.

TABLE I

Computer Generated Quantitative Analysis of the Spectrum of a Methanol Fuel FTP Test

| | Compound | Concentration | Estimated Error of Measurement |
|---|---|---|---|
| 1. | $H_2O$ | 0.27 | 0.1% |
| 2. | $CO_2$ | 0.33 | 0.1% |
| 3. | COHI | 207.65 | 10.0 ppm |
| 4. | HCIC | 14.26 | 8.0 ppmC |
| 5. | NO | 27.74 | 0.3 ppm |
| 6. | $NO_2LO$ | 3.72 | 0.3 ppm |
| 7. | $N_2O$ | −0.01 | 0.1 ppm |
| 8. | HONO | 0.33 | 0.1 ppm |
| 9. | HCN | −0.03 | 0.2 ppm |
| 10. | $NH_3Q$ | −0.06 | 0.1 ppm |
| 11. | $SO_2$ | −0.14 | 0.2 ppm |
| 12. | $CH_4$ | 0.94 | 0.1 ppmC |
| 13. | $C_2H_2$ | −0.36 | 0.2 ppmC |
| 14. | $C_2H_4Q$ | 0.52 | 0.5 ppmC |
| 15. | $C_2H_6$ | 0.06 | 0.2 ppmC |
| 16. | $C_3H_6$ | 0.74 | 1.0 ppmC |
| 17. | $IC_4H_8Q$ | 1.52 | 1.0 ppmC |
| 18. | $CH_2O$ | 6.93 | 0.1 ppmC |
| 19. | HCOOH | −0.08 | 0.1 ppmC |
| 20. | $CH_3OHI$ | 150.98 | 0.1 ppmC |

Total HC = 175.52 ppmC$_3$
Total NOX = 31.79 ppm

We claim:
1. A method of on-line gas analysis of a multicomponent gas emission flow, comprising:
 (a) continuously sequestering a sample flow from said gas emission flow, diluted to lower its dew point to below room temperature, and changed in either temperature and/or pressure to be substantially the same in temperature and pressure as that of gases used to create reference transmission frequency spectral data deployed in step (d);
 (b) continuously irradiating said sample flow with an electromagnetic radiation beam while mounting the amplitude of infrared frequencies in the audio frequency range of said beam, either prior to or immediately subsequent to irradiation of said sample flow, the produce electromagnetic signals having discernible amplitude variations resulting from spectral interference patterns;
 (c) detecting and collecting said signals at a sufficiently high rate to substantially completely distinguish between adjacent spectral pattern amplitude peaks without mutual spectral interference and to permit analysis of said signals and
 (d) analyzing said signals by (i) mathematically manipulating said signals in accordance with Beer's Law to create reformed background-corrected data, and (ii) applying reference transmission frequency spectral data to said reformed data for each suspected gaseous component to give a linear quantitative measure of the presence of each and every suspected gas component in said gas emission flow.
2. The method as in claim 1, in which in step (b) said amplitude modulation is carried out by use of an interferometer 70 to generate spectral interference patterns.
3. The method as in claim 1, in which said step (d)(i) is carried out by taking the negative logarithm of the ratio of corrected known background spectral data to the corrected sample flow transmission spectral data to create reformed data.
4. The method as in claim 1, in which in step (d)(ii) the reference spectral data is in the form of a data mask control which is applied to multiply the data values to retain strong absorption signals while eliminating weak nonabsorbing signals for each suspected gaseous component.

5. The method as in claim 1, in which said quantitative measure of step (d) is rendered within at least four seconds from the irradiation of said sample flow.

6. A method of on-line gas analysis of a multicomponent gas emission flow, comprising:
   (a) continuously sequestering a sample flow from said gas emission flow and affecting the sample flow by (i) filtering to substantially eliminate solid or liquid particles, (ii) diluting to lower its dew point to below room temperature, and (iii) changing said sample flow temperature and pressure to be substantially the same as that used to collect reference transmission frequency spectral data deployed in step (c);
   (b) continuously irradiating the diluted cooled and filtered sample flow with an electromagnetic radation beam, which beam, after having emerged from the sample flow, is split into two parts with one part deviated from the path of the other part to experience a different path length and thence such one part is recombined with said other part in a manner to generate electromagnetic signals resulting from spectral interference patterns;
   (c) detecting and collecting said signals at a minimum of 8000 measurements per each centimeters of path length difference to substantially completely distinguish adjacent spectral pattern peaks without mutual spectral interference; and
   (d) mathematically manipulating the signals to make interference-free by (i) converting an interval of detected and collected signals to base transmission frequency spectrum data, and (ii) applying reference transmission frequency spectral data to said base transmission frequency spectrum data for thereby rendering a concentration per unit time for each and substantially all of the components of the gas emission flow.

7. The method as in claim 6, in which in step (c) said signals are detected and collected during a time interval in which said beam parts experience a minimum of 4 cm of path length difference.

8. The method as in claim 7, in which steep (d) is carried out substantially simultaneously during step (c) in real time.

9. The method as in claim 8, in which the component concentrations per unit time are rendered in an elapsed time of no greater than four seconds after sequestering said sample flow.

10. The method as in claim 6, in which said radiation beam employed in step (b) is infrared.

11. The method as in claim 6, in which in step (a) said sequestered sample flow is taken in a manner to be proportional to the gas emission flow's known mass flow rate.

12. The method as in claim 11, in which the component concentration is divided by the mass flow rate obtained from measuring the exhaust mass flow to thereby provide a mass emission rate per unit of time.

13. The method as in claim 6, in which proportionality of step (a) is achieved by placing a laminar flow element across the main emission flow and placing a similar laminar flow element across the sample flow.

14. The method as in claim 6, in which said dilution is achieved by admitting nitrogen into the sample flow over a ratio range of 5:1 to 70:1.

15. The method as in claim 6, in which said reference absorbance frequency data is masked to contain only the minimum and maximum spectral data frequencies.

16. The method as in claim 6, in which step (d)(i) is carried out by the use of fourier-transform spectroscopic techniques.

17. A method of measuring the multicomponent constituency of a gas emission flow, comprising:
   (a) continuously sequestering a sample flow of said gas emission flow which (i) has been filtered to substantially eliminate solid or liquid particles, (ii) is proportional to the gas emission flow's known mass flow rate, (iii) has been diluted sufficient to lower its dew point to below room temperature, and (iv) has been changed in temperature and pressure to be substantially the same as that used to collect reference transmission frequency spectral data;
   (b) continuously irradiating said diluted sample flow with an infrared electromagnetic radiation beam to generate test spectral data;
   (c) while said steps (a) and (b) are simultaneously proceeding, detecting said test spectral information with a resolution of at least 0.25 cm$^{-1}$; and
   (d) mathematically manipulating the signals to make interference-free by (i) converting an interval of detected signals to base transmission frequency spectral data, and (ii) applying reference transmission frequency spectral data to render a component concentration per unit time.

18. The method as in claim 17, in which said reference transmission frequency spectral data is masked to contain only minimum and maximum data frequencies.

19. The method as in claim 17, in which step (d)(i) is carried out by the use of fourier-transform spectroscopic techniques.

20. The method as in claim 17, in which a tracer gas is introduced at known rate and mixed with said gas emission flow to enable measurement of the mass flow rate of the sample flow.

21. The method as in claim 17, in which in step (d)(ii) the application is carried out by (1) ratioing known background transmission frequency spectral data to base transmission frequency spectral data, (2) taking the negative log of the ratio to create reformed absorbance spectral data, and (3) substrating reference transmission frequency spectral absorbance data, for each suspected component, from the reformed absorbance spectral data to render a component concentration per unit time interval.

22. A gas sampler device, comprising:
   (a) a channel having a length of 3 feet or less and an average aspect ratio (length to diameter) of 24 to 9 for conducting a gas emission flow therethrough between an entrance and exit of said channel;
   (b) means for introducing and mixing a tracer gas at a known rate into said gas emission flow adjacent the entrance thereof;
   (c) means extracting a sample flow from the said channel adjacent the exit thereof which is proportional to the known mass flow rate of said gas emission flow; and
   (d) means for diluting the sample flow with an inert gas to lower its dew point to below room temperature.

23. The device of claim 22, in which said means of (c) comprises a laminar flow element extending across said channel and a similar laminar flow element extending across the sample flow.

24. The device as in claim 22, in which said tracer gas is carbon tetrachloride.

25. An on-line gas measurement apparatus, comprising:

(a) dilution tube means for sequestering a sample flow from a gas emission flow, the sample flow being filtered to substantially eliminate solid or liquid particles, diluted to lower its dew point to below room temperature, and changed in either temperature and/or pressure to be substantially the same in temperature and pressure so that of gases used to create reference transmission frequency spectral data;

(b) FTIR apparatus effective to produce electromagnetic signals with discernibl amplitude variations resulting from irradiating said sample flow;

(c) computer means for (i) detecting and collecting said signals at a sufficiently high rate to substantially completely distinguish between adjacent spectral amplitudes without mutual spectral interference, and (ii) analyzing said signals in accordance with Beer's Law to create reformed background-corrected data and applying reference transmission frequency spectral data to said reformed data for each suspected gas component to give an linear quantitative measure of the presence of each and every suspected gas component in said gas emission flow.

* * * * *

UNITED STATES PATENT AND TRADEMARK OFFICE
CERTIFICATE OF CORRECTION

PATENT NO.   : 4,801,805

DATED        : January 31, 1989

INVENTOR(S)  : James W. Butler, Paul D. Maker, Thomas J. Korniski, Alex D. Colvin It is certified that error appears in the above-identified patent and that said Letters Patent is hereby corrected as shown below:

Delete claims 22, 23, 24 and 25 in their entirety.

On the title page, "25 Claims" should read -- 21 Claims --.

Signed and Sealed this

Fourth Day of July, 1989

Attest:

DONALD J. QUIGG

Attesting Officer

Commissioner of Patents and Trademarks